(12) United States Patent
Li et al.

(10) Patent No.: US 11,285,278 B2
(45) Date of Patent: Mar. 29, 2022

(54) E-JUICE DRIPPING TYPE ATOMIZER IN ELECTRONIC CIGARETTE HAVING U-SHAPED AIRFLOW CHANNEL

(71) Applicant: CHINA TOBACCO YUNNAN INDUSTRIAL CO., LTD, Kunming (CN)

(72) Inventors: Zhiqiang Li, Kunming (CN); Shanzhai Shang, Kunming (CN); Ping Lei, Kunming (CN); Jingmei Han, Kunming (CN); Chengya Wang, Kunming (CN); Ru Wang, Kunming (CN); Xu Zeng, Kunming (CN); Dong Xiao, Kunming (CN); Dalin Yuan, Kunming (CN); Lingxuan Liu, Kunming (CN); Nengjun Xiang, Kunming (CN); Lei Wang, Kunming (CN); Yongkuan Chen, Kunming (CN)

(73) Assignee: CHINA TOBACCO YUNNAN INDUSTRIAL CO., LTD, Kunming (CN)

( * ) Notice: Subject to any disclaimer, the term of this patent is extended or adjusted under 35 U.S.C. 154(b) by 420 days.

(21) Appl. No.: 16/455,760

(22) Filed: Jun. 28, 2019

(65) Prior Publication Data

US 2019/0336708 A1    Nov. 7, 2019

(30) Foreign Application Priority Data

May 4, 2018    (CN) .......................... 201810435629.7

(51) Int. Cl.
*A24F 13/00* (2006.01)
*A24F 17/00* (2006.01)
(Continued)

(52) U.S. Cl.
CPC ............... *A61M 15/06* (2013.01); *A24D 3/17* (2020.01); *A24F 40/42* (2020.01); *A24F 40/48* (2020.01);
(Continued)

(58) Field of Classification Search
CPC .......... A24F 40/10; A24F 40/42; A24F 40/48; A24F 40/485; A24F 40/60; A61M 11/042; A61M 15/06; A24D 3/17
See application file for complete search history.

(56) References Cited

U.S. PATENT DOCUMENTS

| | | | | |
|---|---|---|---|---|
| 4,911,181 A | * | 3/1990 | Vromen ................... | A24F 42/20 131/273 |
| 5,113,878 A | * | 5/1992 | Polese ..................... | A24F 13/04 131/198.2 |

(Continued)

*Primary Examiner* — Abdullah A Riyami
*Assistant Examiner* — Thang H Nguyen
(74) *Attorney, Agent, or Firm* — Bayramoglu Law Offices LLC

(57) ABSTRACT

An e-juice dripping type atomizer includes an e-juice storage tank, wherein a sealed surface of the e-juice storage tank is provided with at least one oil-dropping hole, a piston cylinder is sleeved in an opening of the e-juice storage tank, a piston rod is provided in the piston cylinder, an upper part of the piston rod is detachably connected to a cigarette filter; and a heating wire located at an outlet of an oil-dropping hole. An inner tank and an outer tank are provided outside the e-juice storage tank and the heating wire. The outer tank is fixedly connected to an atomizing outer tube. A side wall of the atomizing outer tube is provided with an air inlet hole. A gap enclosed by air inlet hole, inner tank and outer tank and a gap between e-juice storage tank and inner tank define a U-shaped airflow channel.

5 Claims, 4 Drawing Sheets

(51) Int. Cl.
*A24F 25/00* (2006.01)
*A61M 15/06* (2006.01)
*A61M 11/04* (2006.01)
*A24D 3/17* (2020.01)
*A24F 40/42* (2020.01)
*A24F 40/48* (2020.01)
*A24F 40/485* (2020.01)
*A24F 40/60* (2020.01)
*A24F 40/10* (2020.01)

(52) U.S. Cl.
CPC ............ *A24F 40/485* (2020.01); *A24F 40/60* (2020.01); *A61M 11/042* (2014.02); *A24F 40/10* (2020.01)

(56) References Cited

U.S. PATENT DOCUMENTS

| | | | |
|---|---|---|---|
| 10,092,037 B2 * | 10/2018 | Tucker | A61M 15/06 |
| 2005/0224136 A1 * | 10/2005 | Hayes | A24F 25/00 |
| | | | 141/329 |
| 2006/0196518 A1 * | 9/2006 | Hon | H05B 1/0244 |
| | | | 131/360 |
| 2008/0230052 A1 * | 9/2008 | Montaser | A61M 11/042 |
| | | | 128/200.16 |
| 2017/0157341 A1 * | 6/2017 | Pandya | A61M 11/005 |
| 2018/0000156 A1 * | 1/2018 | Qiu | A24F 40/40 |
| 2018/0249762 A1 * | 9/2018 | Daryani | A24F 40/48 |
| 2019/0174831 A1 * | 6/2019 | Qiu | A61M 15/06 |
| 2020/0337382 A1 * | 10/2020 | Sur | A61M 11/042 |
| 2020/0383383 A1 * | 12/2020 | Fornarelli | F16K 1/46 |
| 2021/0015158 A1 * | 1/2021 | Moloney | A24F 40/50 |
| 2021/0219617 A1 * | 7/2021 | Lee | H05B 6/108 |

\* cited by examiner

E-JUICE DRIPPING TYPE ATOMIZER IN ELECTRONIC CIGARETTE HAVING U-SHAPED AIRFLOW CHANNEL

CROSS REFERENCE TO THE RELATED APPLICATIONS

This application is based upon and claims priority to Chinese Patent Application No. 201810435629.7, filed on May 4, 2018, the entire contents of which are incorporated herein by reference.

TECHNICAL FIELD

The present invention belongs to the field of electronic cigarettes, particularly relates to an e-juice dripping type atomizer in the field of electronic cigarettes.

BACKGROUND

Electronic cigarettes, as one of the alternative tobacco products, are gradually obtaining an acceptance of vast number of consumers. Thereinto, the electronic cigarette with e-juice injection type atomizer is popular among many smokers, because e-juice of different flavors can be injected as needed, leading to broader choice, and the high volume of smoke fully satisfies the consumers physically.

The key technology of the electronic cigarette is the design of the atomizer. In the prior art, it is common to introduce the e-juice in an e-juice tank onto a heating wire through a guide oil cotton. The e-juice is heated and atomized on the heating wire to generate smoke.

The drawbacks widely existing in the existing atomizers are as below. The e-juice is stored in a non-hermetic environment, and the e-juice in the e-juice tank is in a large-area contact with air, tending to cause the oxidation of e-juice, thereby affecting the quality of the e-juice, and greatly reducing the smoking experience. In addition, when the atomizer is placed sideways or reversely, e-juice leaking phenomenon is readily to occur. Moreover, since the viscosity of the e-juice is relatively large, the inlet hole is prone to be blocked. The way to address this issue is complicated and hard to operate, and during the operation, the e-juice is very likely to overflow, thus contaminating using environment.

The prior art has other drawbacks as follows.

1. There are excessive injection holes and guild oil cotton inserting holes, and the highest surfaces of the holes are not in a same plane. Consequently, the e-juice may readily flow out from other holes except for the injection holes when injecting the e-juice;

2. The hole diameter of the injection hole is a bit small due to the limitation of the structure and size. Since the e-juice is a highly viscous liquid with a large surface tension, the injection hole is readily blocked, causing a failure of e-juice injection. The way to solve this issue is complicated and has poor operability. Moreover, the e-juice overflows readily during operation to pollute using environment;

3. The e-juice is delivered from bottom to top through the guild oil cotton. With the consumption of the e-juice during the operation, the liquid level of the e-juice changes to make an oil guide effect variable, causing a variation of the oil guide volume, affecting an atomizing effect of the atomizer, and entailing impacts on consumers' experience of the smoke volume and flavor;

4. When the storage volume of the e-juice is low or pretty low, the guide oil cotton cannot deliver all of the e-juice to the atomizer base, which tends to cause heating without liquid. Besides, a small amount of the remaining e-juice should be completely removed when replacing different kinds of e-juice. The operating process is complicated and wastes the e-juice;

5. The atomizer base is close to the cigarette filter, the heater is provided above the atomizer base and closer to the cigarette filter, and a heat transfer between the heater and the cigarette filter and the high-temperature smoke may burn users' mouth;

6. Because of the limitation of the structure, an air inlet channel and the heater are basically on a same plane, or the air inlet channel is a bit lower than the heater. Besides, this type of air inlet channel has a relatively small inlet hole, so the inhaled air cannot take most of the smoke produced by atomization away, resulting in that the accumulated heat burns out the guild oil cotton. Moreover, the e-juice delivered to the heater is prone to leaking through the air inlet holes.

7. The atomization process of the atomizer is not observable, and actions cannot be taken in time when an abnormal situation occurs during use.

The objective of the present invention is to solve the above-mentioned problems.

SUMMARY

The present invention provides an e-juice dripping type atomizer which includes:

an e-juice storage tank, wherein a sealed surface at a lower end of the e-juice storage tank is provided with at least one oil-dropping hole; a piston cylinder is sleeved in an opening of an upper end of the e-juice storage tank; a piston rod is provided in the piston cylinder, and an upper part of the piston rod is detachably connected to a cigarette filter; and a heating wire located at an outlet of the oil-dropping hole.

Specifically, when the piston rod moves downward, the air above an e-juice in the e-juice storage tank will be compressed and pressurized, thereby pushing the e-juice gradually to drip through the oil-dropping hole at a bottom of the e-juice storage tank. Preferably, the piston rod is provided with a scale to show a movement of the e-juice, assisting users to check and control an oil-dropping amount.

Preferably, an inner tank and an outer tank are successively provided outside the e-juice storage tank and the heating wire. The outer tank is fixedly connected to an atomizing outer tube. A side wall of the atomizing outer tube is provided with an air inlet hole. A gap enclosed by the air inlet hole, the inner tank and the outer tank and a gap between the e-juice storage tank and the inner tank collectively define a U-shaped airflow channel accessed to the cigarette filter eventually.

Preferably, the cigarette filter is fixed on a top of the outer tank through a cigarette filter base. The cigarette filter base is provided with an arc-shaped vent hole configured to connect the U-shaped airflow channel to the cigarette filter.

Preferably, a gas adjusting ring is sleeved outside the air inlet hole. An overlap area between the gas adjusting ring and the air inlet hole is adjustable, so as to adjust an air inflow.

Preferably, the piston rod is contained in a cigarette filter cap. An elastic mechanism is provided inside the cigarette filter cap. An end of the elastic mechanism abuts against a lower surface of the cigarette filter, and the other end of the elastic mechanism abuts against an upper surface of the cigarette filter base.

Preferably, the inner tank and the outer tank are all or partially transparent.

The present invention has the following advantages.

1. The e-juice storage tank is airtight. The e-juice storage tank is hermetic as a whole except for the oil-dropping hole at the bottom of the e-juice storage tank contacting air, minimizing a contact area between the e-juice and air, and prolonging the e-juice storage time.

2. Extremely small oil-dropping holes are provided at the bottom of the e-juice storage tank, and the e-juice can drip from the oil-dropping hole only by applying external force to push the piston rod from the top of the e-juice storage tank. Without pushing the piston, whatever angle the atomizer is placed at, the e-juice will not leak out, which basically eliminates oil leakage phenomenon.

3. Precisely control the oil-dropping amount: the volume of e-juice employed for each time is adjusted and controlled by observing the scale on the piston rod, the volume of e-juice used for each time is controllable, and the use process is convenient.

4. The design of the U-shaped airflow channel has the following advantages. When air flows between the outer tank and the inner tank via the air inlet hole, the outer tank and the inner tank may be cooled down to reduce the temperature of the outer tank to avoid hands being burnt. When the air carrying the smoke produced by the heating wire flows between the inner tank and the e-juice storage tank, the e-juice storage tank storing a large amount of e-juice functions as a cooling device capable of reducing the temperature of the smoke, thus preventing the smoke from burning users' mouth. Moreover, the e-juice condensed on an outer wall of the e-juice storage tank can flow back to the heating wire for recycling.

5. The atomization effect will not be affected by the e-juice storage amount. The oil-dropping hole of the e-juice storage tank is located at the bottom of the e-juice storage tank. The volume of e-juice employed by pushing and compressing the piston rod for each time is not affected by the e-juice storage amount, thereby not affecting the atomization effect.

6. The inner tank and the outer tank are all or partially transparent, so the users can conveniently observe the atomization process of the whole heater from the outside, mastering the operating state of the atomizer in real time, so as to correspondingly take reasonable actions in time.

Figure 1:
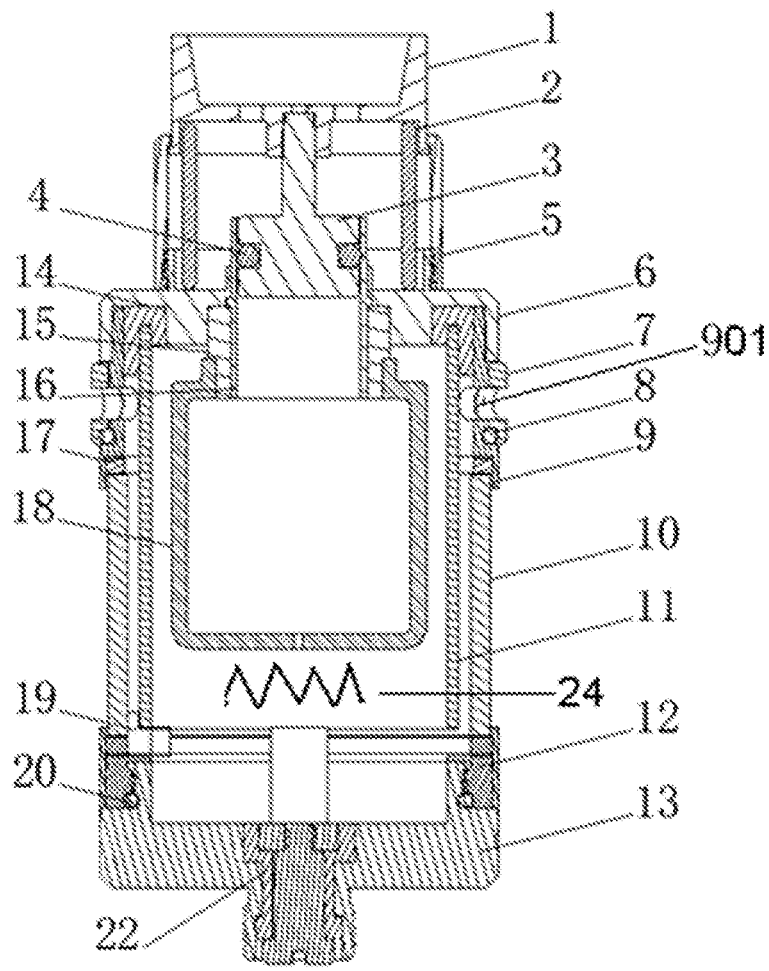
FIG. 1 is a sectional view of an e-juice dripping type atomizer of the present invention.
Figure 2:
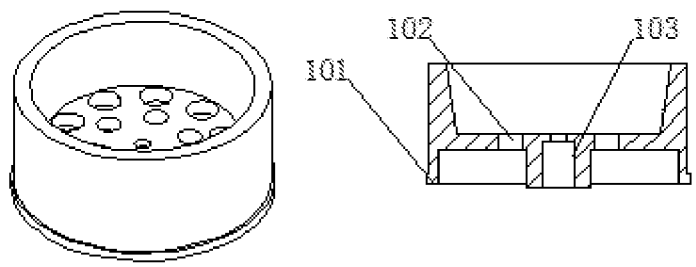
FIG. 2 is a schematic diagram showing a cigarette filter.
Figure 3:
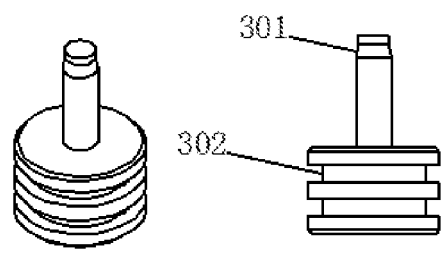
FIG. 3 is a schematic diagram showing a piston rod.
Figure 4:
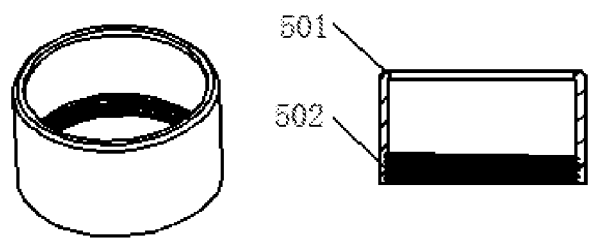
FIG. 4 is a schematic diagram showing a cigarette filter cap.
Figure 5:
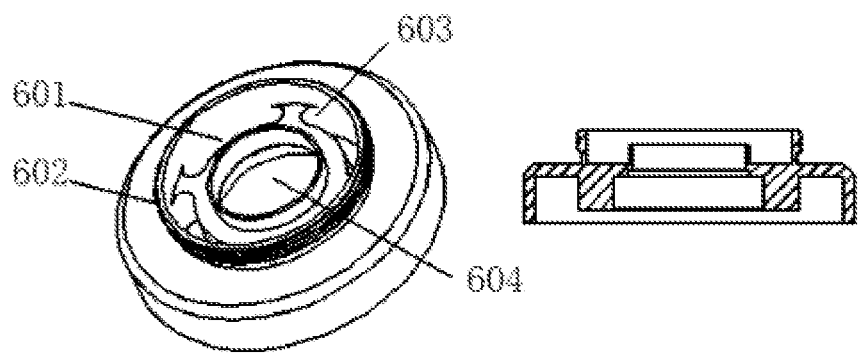
FIG. 5 is a schematic diagram showing a cigarette filter base.
Figure 6:
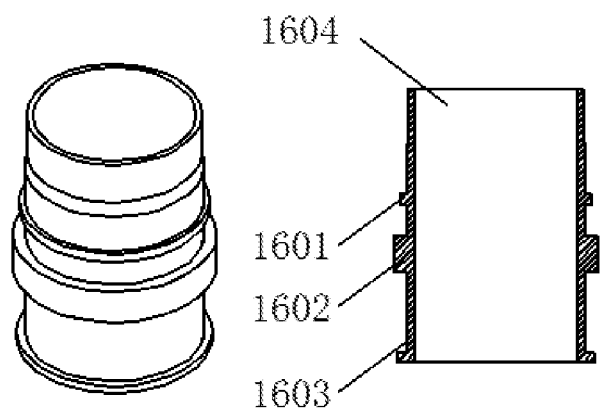
FIG. 6 is a schematic diagram showing a piston cylinder.
Figure 7:
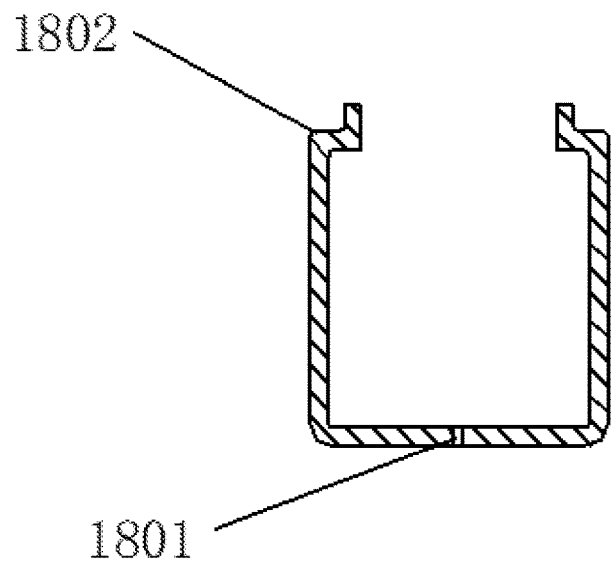
FIG. 7 is a schematic diagram showing an e-juice storage tank.
Figure 8:
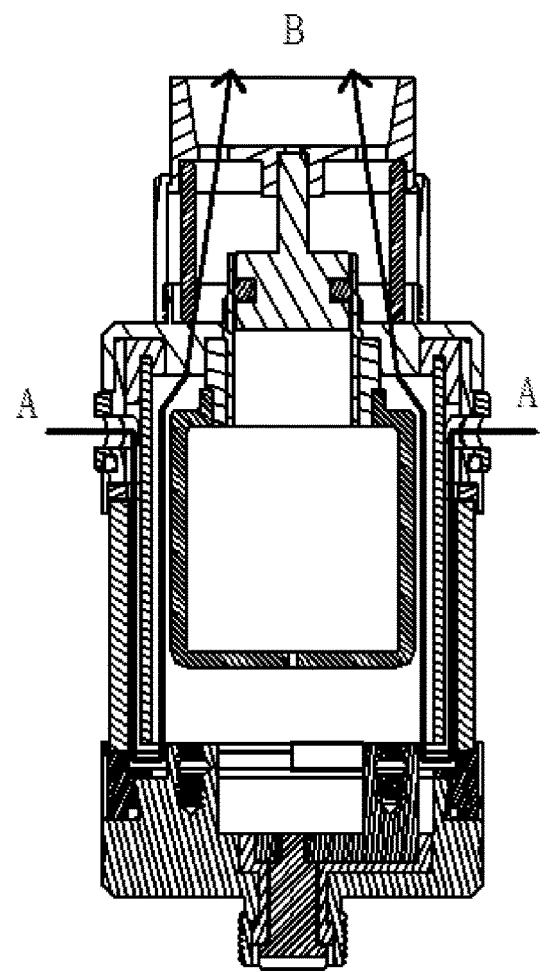
FIG. 8 is a schematic diagram showing a U-shaped airflow channel.
Figure 9:
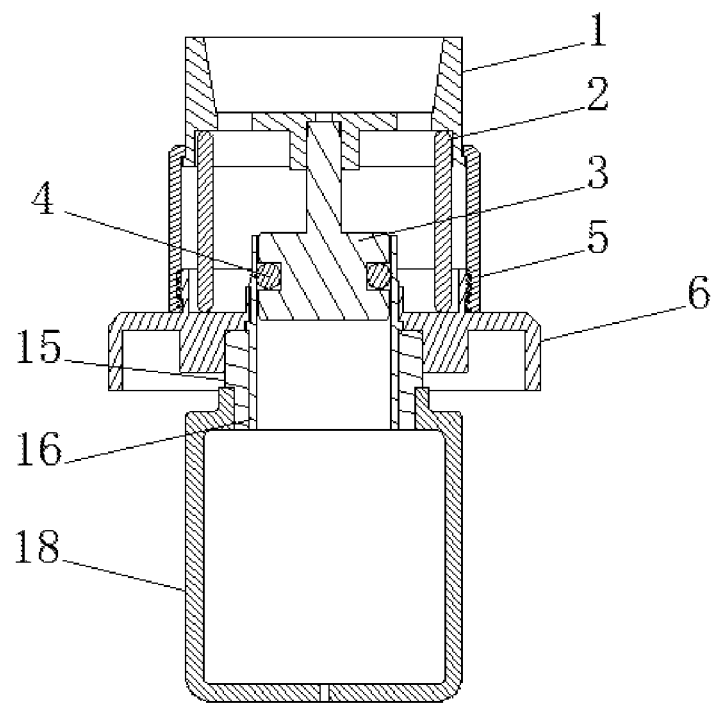
FIG. 9 is a structural schematic diagram showing an e-juice dripping type atomizer before a piston rod is pushed.
Figure 10:
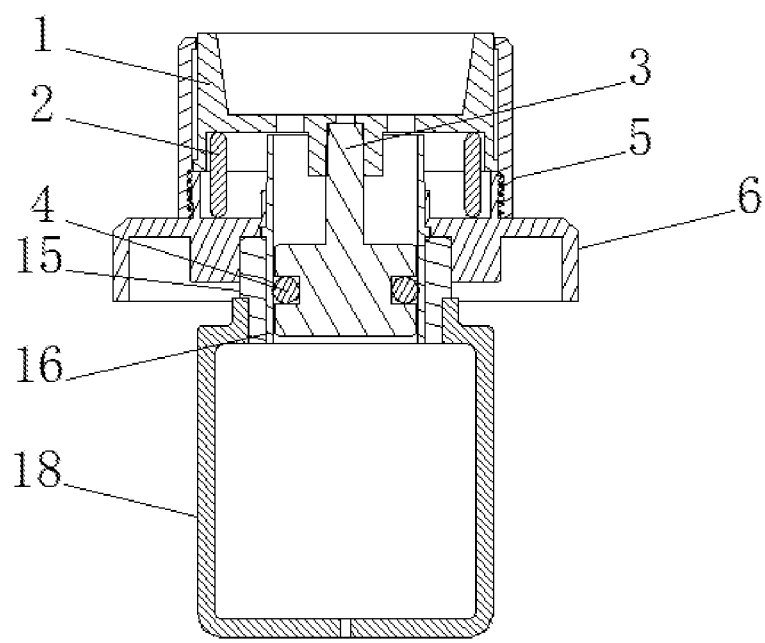
FIG. 10 is a structural schematic diagram showing an e-juice dripping type atomizer after a piston rod is pushed.

The reference designators in the drawings are described below:

1: cigarette filter, 2: elastic mechanism, 3: piston rod, 4: I-type O-shaped ring, 5: cigarette filter cap, 6: cigarette filter base, 7: gas adjusting ring, 8: II-type O-shaped ring, 9, atomizing outer tube, 10: outer tank, 11: inner tank, 12, reinforce ring, 13: atomizer base, 14: III-type O-shaped ring, 15: sealing mechanism, 16: piston cylinder, 17: IV-type O-shaped ring, 18: e-juice storage tank, 19: V-type O-shaped ring, 20: VI-type O-shaped ring, 22: insulation ring, 24: heating wire, 101: cigarette filter limit, 102: cigarette filter air inlet hole, 103: piston groove, 301: piston guiding rod, 302: piston rod annular groove, 501: limit casing, 502: cigarette filter cap thread, 601: cigarette filter base inner ring, 602: cigarette filter base outer ring thread, 603: arc-shaped vent hole, 604: piston cylinder opening, 901: air inlet hole, 1601: upper limit, 1602: lower limit, 1603: piston protruded ring, 1604: piston channel, 1801: oil-dropping hole, 1802: e-juice storage tank opening.

DETAILED DESCRIPTION OF THE EMBODIMENTS

The present invention will be further described hereinafter with reference to the drawings. The following embodiments are merely intended to explain the technical solution of the present invention more clearly, rather than limit the scope of the present invention.

The e-juice dripping type atomizer of the present invention mainly includes the following components:

the cigarette filter 1 having a cylinder-like shape, wherein a plurality of the cigarette filter air inlet holes 102 are provided on a horizontal plane perpendicular to a cylinder surface and close to a bottom of the cigarette filter; a geometric center of the horizontal plane is provided with the cylindrical piston groove 103 facing downward and having a diameter less than the cigarette filter 1; a bottom of the cylindrical piston groove and the bottom of the cigarette filter are on a same horizontal plane; the cylindrical piston groove is configured to contain the piston guiding rod 301 of the piston rod 3 described as below; and the bottom of the cigarette filter 1 is provided with the cigarette filter limit 101;

the elastic mechanism 2; wherein the elastic mechanism may be a spring coil, and two ends thereof respectively abut against a lower surface of the cigarette filter 1 and an upper surface of the cigarette filter base 6 described as below; the mission of the elastic mechanism 2 is to be compressed to store energy when a user pushes the piston rod 3, and to return to its original shape when the user stops pushing the piston rod 3, facilitating a reset effect of the piston rod;

the piston rod 3 presenting an inverted T shape as a whole, and a cylinder-like shape at the upper and lower parts; wherein the upper part of the piston rod is the piston guiding rod 301 having a diameter less than the lower part of the piston rod; and the lower part of the piston rod is evenly provided with the piston rod annular grooves 302;

the cigarette filter cap 5 having a cylinder-like shape, wherein an upper part of the cigarette filter cap is provided with the limit casing 501 extending inward, and an inner side of a lower part of the cigarette filter cap is provided with the cigarette filter cap thread 502;

the cigarette filter bases 6 having an annular shape, wherein the cigarette filter bases includes the cigarette filter base inner ring 601 and the cigarette filter base outer ring 602, and the arc-shaped cigarette filter base vent holes 603 are evenly provided between the cigarette filter base inner ring and the cigarette filter base outer ring;

the piston cylinder 16 having a cylinder-like shape, wherein a periphery of the piston cylinder is provided with protruded rings of different heights, the piston cylinder includes the upper limit 1601, the lower limit 1602, the piston protruded ring 1603 and the piston channel 1604; and the e-juice storage tank 18 having a cup-like shape, wherein an upper part of the e-juice storage tank is provided with the e-juice storage tank opening 1802 having a large opening, the piston cylinder 16 is sleeved in the e-juice storage tank opening, and a lower part of the e-juice storage tank 18 is provided with at least one oil-dropping hole 1801.

Connections between the various components are:

The piston guiding rod 301 of the piston rod 3 is inserted into the piston groove 103 of the cigarette filter 1 by riveting. The piston rod annular groove 302 is used to replace the I-type O-shaped ring 4. The lower part of the piston rod 3 may be inserted into the piston channel 1604, and may move therein upward and downward. The use of the I-type O-shaped ring 4 increases the frictional force, reduces the rigid strength, and further reduces the abrasion of the piston channel 1604.

The cigarette filter cap 5 is directly sleeved outside the periphery of the cigarette filter 1, wherein the limit casing 501 of the cigarette filter cap 5 and the cigarette filter limit 101 of the cigarette filter 1 abut against each other to prevent the cigarette filter 1 from popping up and falling down when the elastic mechanism 2 resets. The cigarette filter cap thread 502 is in a clearance fit with the cigarette filter base outer ring thread 602 for a threaded connection.

The piston rod 3 is put into the elastic mechanism 2. An upper part of the elastic mechanism 2 directly abuts against a lower part of the plane where the cigarette filter air inlet hole is located. A lower part of the elastic mechanism 2 abuts against a bottom surface of the cigarette filter base 6.

The piston cylinder 16 is located on the lower part of the cigarette filter base 6. An upper part of the piston cylinder 16 penetrates outward through the piston cylinder opening 604. The upper limit 1601 prevents the cigarette filter 6 from keeping moving downward. The sealing mechanism is placed between the lower limit 1602 and the piston protruded ring 1603, which makes the lower part of the piston cylinder 16 connected to the e-juice storage tank opening 1802 of the e-juice storage tank 18.

The working principle of the present invention is as follows. During smoking, the cigarette filter 1 is compressed to make the piston rod 3 move downward, thus pushing air in the e-juice storage tank 18 to increase the pressure intensity in the e-juice storage tank. The e-juice stored in the e-juice storage tank is pushed to drip through the oil-dropping hole 1801, and drops onto the heating wire below (it is merely shown schematically, and the specific electric connection is omitted). The e-juice is heated and atomized. The amount of e-juice for atomization may be selected as needed. When the cigarette filter 1 is released, the applied force disappears, the elastic mechanism 2 resets, the piston rod 3 resets, the air pressure in the e-juice storage tank 18 restores balance, and the e-juice stops to drop down, without affecting normal smoking. In work, airflow enters through the gas adjusting ring 7 via the air inlet hole 901, passes downward through a gap between the inner wall of the outer tank and the outer wall of the inner tank to the heating wire 24 at the bottom, then turns back from the bottom upward to pass through a gap between the outer wall of the e-juice storage tank and the inner wall of the inner tank to arrive at the cigarette filter vent hole 603, and eventually is inhaled into the user's mouth through the cigarette filter air inlet hole 102.

What is claimed is:

1. An e-juice dripping type atomizer, comprising:
   an e-juice storage tank, wherein a surface of a lower end of the e-juice storage tank is provided with at least one oil-dropping hole, a piston cylinder is sleeved in an opening of an upper end of the e-juice storage tank, a piston rod is provided in the piston cylinder, an upper part of the piston rod is detachably connected to a cigarette filter; and
   a heating wire located at an outlet of the at least one oil-dropping hole;
   wherein an inner tank and an outer tank are successively provided outside the e-juice storage tank and the heating wire, the outer tank is fixedly connected to an atomizing outer tube, a side wall of the atomizing outer tube is provided with an air inlet hole, a gap enclosed by the air inlet hole, the inner tank, and the outer tank and a gap between the e-juice storage tank and the inner tank collectively define a U-shaped airflow channel eventually accessed to the cigarette filter.

2. The e-juice dripping type atomizer according to claim 1, wherein the cigarette filter is fixed on a top of the outer tank through a cigarette filter base, the cigarette filter base is provided with a plurality of arc-shaped vent holes configured to connect the U-shaped airflow channel to the cigarette filter.

3. The e-juice dripping type atomizer according to claim 1, wherein a gas adjusting ring is sleeved outside the air inlet hole, an overlap area between the gas adjusting ring and the air inlet hole is adjustable for adjusting an air inflow.

4. The e-juice dripping type atomizer according to claim 2, the piston rod is contained in a cigarette filter cap, an elastic mechanism is provided inside the cigarette filter cap, a first end of the elastic mechanism abuts against a lower surface of the cigarette filter, and a second end of the elastic mechanism abuts against an upper surface of the cigarette filter base.

5. The e-juice dripping type atomizer according to claim 1, wherein the inner tank and the outer tank are all or partially transparent.

* * * * *